United States Patent [19]

Törnblom

[11] Patent Number: 4,945,307

[45] Date of Patent: Jul. 31, 1990

[54] ELECTRONIC DEVICE FOR DETECTING IRREGULARITIES IN A SURFACE OF A SOLID OBJECT

[75] Inventor: Bengt Törnblom, Västerås, Sweden

[73] Assignee: Törnbloms Kvalitetskontroll AB, Västerås, Sweden

[21] Appl. No.: 926,850

[22] Filed: Nov. 3, 1986

Related U.S. Application Data

[63] Continuation of Ser. No. 621,916, filed as PCT SE83/00409 on Nov. 22, 1983, published as WO84/02189 on Jun. 7, 1984, abandoned.

[30] Foreign Application Priority Data

Nov. 24, 1982 [SE] Sweden .................... 8206678

[51] Int. Cl.⁵ .................. G01N 27/90; G01R 33/12
[52] U.S. Cl. .................................. 324/225; 324/237
[58] Field of Search ............ 324/225, 226, 207, 208, 324/202, 233, 234–240, 260–262; 328/163, 165, 162; 307/358, 520; 455/304; 246/249; 330/149

[56] References Cited

U.S. PATENT DOCUMENTS

| | | | |
|---|---|---|---|
| 3,391,389 | 7/1968 | Cruger et al. | 307/520 X |
| 3,588,534 | 6/1971 | Campbell et al. | 307/520 |
| 3,870,996 | 3/1975 | Miller | 455/304 X |
| 3,906,384 | 9/1975 | Schiffman | 328/165 |
| 4,112,381 | 9/1978 | Mortensen et al. | 307/520 X |
| 4,175,256 | 11/1979 | Dolikian | 307/358 X |
| 4,255,709 | 3/1981 | Zatsepin et al. | 324/229 |
| 4,325,068 | 4/1982 | Mercer | 455/304 X |
| 4,339,727 | 7/1982 | Kage et al. | 307/358 X |
| 4,368,429 | 1/1983 | Jamison | 324/225 |
| 4,492,928 | 1/1985 | Hayakawa et al. | 307/520 X |
| 4,496,859 | 1/1985 | Crooks | 307/520 |

FOREIGN PATENT DOCUMENTS

| | | |
|---|---|---|
| 7201970 | 6/1975 | Sweden . |
| 75078576 | 5/1977 | Sweden . |
| 76137082 | 5/1982 | Sweden . |
| 652479 | 3/1979 | U.S.S.R. . |
| 2041535 | 9/1980 | United Kingdom . |

OTHER PUBLICATIONS

D. D. Buss et al., "Transversal Filtering Using Charger-Transfer Devices" in IEEE Journal of Solid-State Circuits, vol. Sc-8, No. 2, Apr. 1973.

Primary Examiner—Reinhard J. Eisenzopf
Assistant Examiner—W. Edmonds
Attorney, Agent, or Firm—Watson Cole Grindle & Watson

[57] ABSTRACT

A device for detecting irregularities in the surface of an object comprises at least one transducer which is movable relative to the surface of the object and an associated signal-processing unit which receives and processes output signals generated by the transducer. The signal-processing unit includes two electrical circuits, the first circuit providing a signal A which is derived from the output signal from the transducer and the second circuit including an analog shift register to provide a signal B which is derived from the output signal from the transducer and which is time delayed relative to signal A. The signal-processing unit also includes means for combining signals A and B to provide a measuring signal C.

12 Claims, 1 Drawing Sheet

ELECTRONIC DEVICE FOR DETECTING IRREGULARITIES IN A SURFACE OF A SOLID OBJECT

This application is a continuation, of application Ser. No. 621,916, filed as PCT SE83/00409 on Nov. 12, 1983, published as WO84/02189 on Jun. 7, 1984, now abandoned.

BACKGROUND OF THE INVENTION

The invention relates to a device for measuring and/or control, for example, testing, of materials such as bodies, liquids, powders, billets, tubes, rods, wire, etc., with respect to changes/irregularities, as for example defects and so on, in or on the material.

The invention is intended to be used within technical fields such as eddy current testing, ultrasonic testing, leakage flux testing, and so on, that is, NDT techniques normally occurring in industry.

For simplicity, the description will be restricted, in the following, to the eddy current field in spite of the fact that the invention has a considerably wider and more general field of application, which is thus to be understood in the following.

The majority of the measuring and/or control devices available on the market can be described as transducers with subsequent signal processing and output circuits. The signals which are obtained from these transducers are often very difficult to signal process in an efficient manner because of their shape and duration. As an example, the detected transducer signal may consist of a simple half-period pulse, which is difficult to separate from undesired signals which, unfortunately, are too often present.

SUMMARY OF THE INVENTION

The present invention discloses a simple and fundamentally refined method of drastically improving the signal processing possibilities by utilizing time lag/signal delay of one or several signals which directly or indirectly is/are derived from the transducer.

A patent application of a complementary kind is disclosed in Swedish patent application No. 7813344-4.

Swedish patents Nos. 7507857-6 and 7613708-2 can be improved to a considerable extent with respect to performance by utilizing the present invention.

The invention, which aims to provide a solution to the problems mentioned above and other problems associated therewith, will be described in the following. A device according the invention can be described as a device for control and/or measurement of materials with respect to changes/irregularities in/on the material, the device comprising at least one scanning member/transducer for scanning/sensing the material or a part thereof, and at least one signal processing part/circuit, for example electronic equipment, directly or indirectly associated with the noted member, for signal processing of signals derived from the transducer, utilizing at least one signal-delay function/circuit, for example a shift register and characterized in that at least two signals, mutually time-delayed, directly or indirectly originating from the same change/irregularity, are combined, for example weighted and summed in such a way that the change/irregularity can be detected in a better way.

The term "combined" also comprises the case where, for example, the signals A and B in FIG. 1, in addition to being mutually time-delayed, are signal-processed individually or together via, for example, a filter. This very fact, that is, using signal delay and active filters, has proved very efficient in pratice, since in that way the filter characteristic suppresses undesired signals considerably whereas, for example, the defect is emphasized. In other words, there is a great variety of possibilities of performing the signal processing.

In practice, transducers are often designed as absolute or differential (balanced) transducers. The absolute transducers have special advantages with regard to measuring practice but normally provide a half-period pulse when, for example, a defect passes the transducer, as opposed to the differential transducers which then provides a complete full-period pulse, which is much more simple to signal-process. Characteristic of the present invention is that with, for example, the absolute transducer as a starting point, a signal of a differential nature is simulated, while at the same time retaining the advantages of the absolute transducer. This means that with one simple transducer, the advantages of both transducer types can be utilized, which is a great advantage from the point of view of measuring practice.

DESCRIPTION OF THE DRAWINGS

As an example, a simple but very practicable embodiment of the present invention is shown in greatly simplified form in FIG. 1.

DETAILED DESCRIPTION OF THE PREFERRED EMBODIMENT

Figure 1:
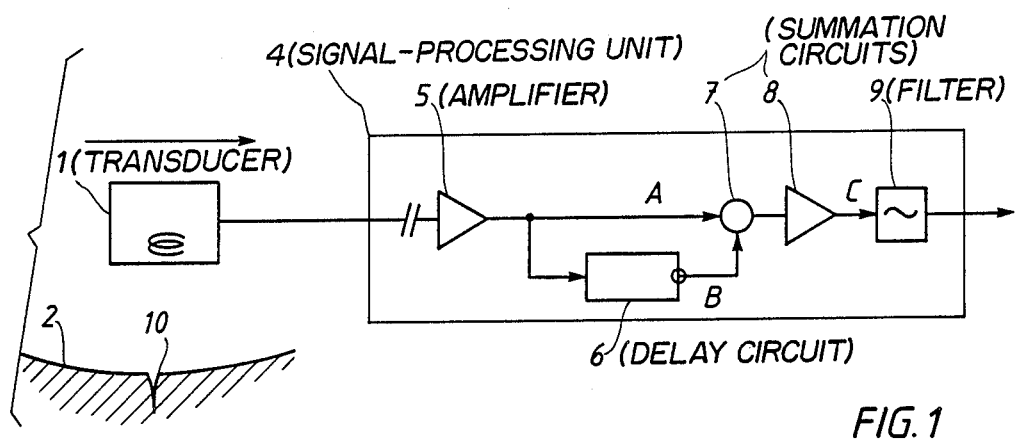
Figure 2:
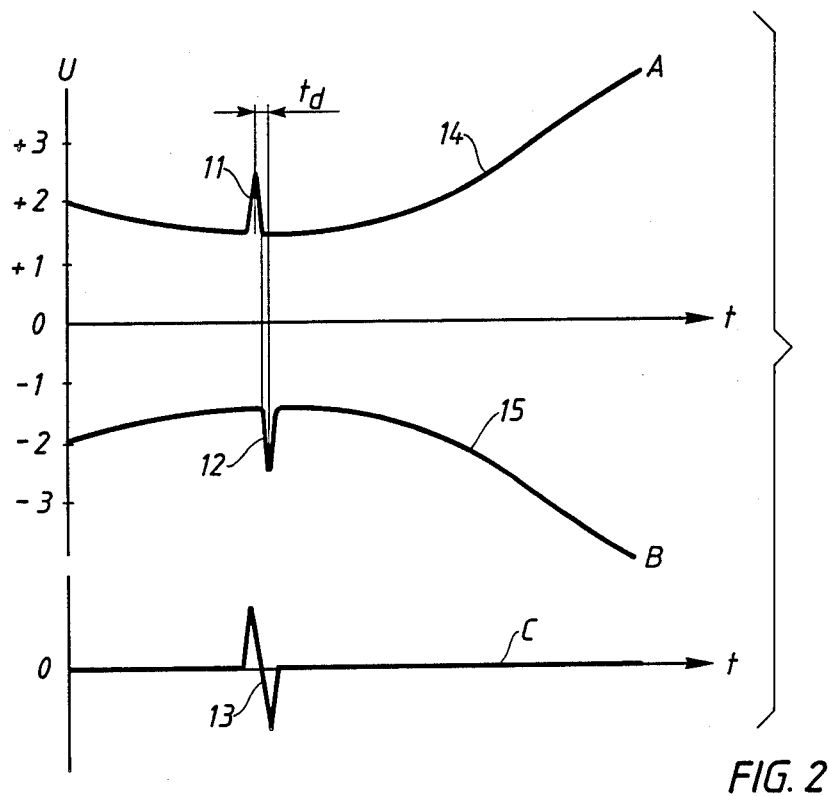
FIG. 2 shows the singals A, B and C, which refer to signals A, B and C in FIG. 1 and are derived from the transducer and thereby also wholly or partially from the object.

FIG. 1, which thus is a simplified block diagram, shows the transducer (1) moving over, for example, a hot billet surface (2) in which there is a defect/crack (10) that is to be detected/measured. From the transducer, signals are emitted to a subsequent signal processing unit (4), comprising certain signal-processing circuits as, for example, an amplifier (5), a delay circuit (6), a summation circuit (7, 8) and a filter (9). When the transducer moves over the billet surface, or when the billet or the transducer vibrates, the distance between the transducer and the billet surface often varies. This gives rise to undesired disturbing signals which considerably deteriorate the possibilities of detection. Signal A in FIG. 1 may, for example, be an amplified, rectified and prefiltered carrier frequency signal from the transducer, the appearance of which may be as shown is FIG. 2. The low-frequency inclination (14) is due to the curving of the billet surface (2), whereas the more high-frequency pulse superimposition (11) is related to the defect (10). By delaying the signal A in the signal-delay circuit (6) in FIG. 1, the signal B is obtained, the appearance of which is shown in FIG. 2. As can be seen, signal B has reversed polarity and is delayed by the time $t_d$.

If the signals A and B are summed, as in FIG. 1, by means of, for example, a summational amplifier (7, 8), the signal C is obtained, which is shown at the bottom of FIG. 2. It can now be seen that the fault signal (11) and (12), respectively, originating from the defect has been combined so that a complete sine period (13) has been superimposed on the signal C. On the other hand, the low-frequency signal components in A (14) and B (15), respectively, have been greatly suppressed. In this way, the chances of an efficient separation/filtering of the fault signal have been significantly increased.

In Fig. 1, the signal C is further filtered in a filter (9), which is adjusted to the frequency contents of the fault signal (13).

It should be pointed out here that the time-lag delay ($t_d$) of the delay circuit (6) has an optimum value related to the appearance and duration of the fault pulse.

The advantages of the invention described here in relation to only ordinary active filters reside in the fact that the filter effect is not connected to the Q-factors, etc., of filters, which deteriorate the pulse response.

Within the scope of the invention, the optimum location of the signal delay may, of course, vary in dependence on the desired function, application and construction. Also, the invention is applicable to the suppression of a highly varying range of undesired signals, etc., provided the frequency contents are suitable. It is also possible to extend the number of delay circuits and thereby obtain a greater number of signals to combine, thus to a corresponding degree improving the measuring and detection possibilities.

An example of how the present device/invention can be combined in practice with other inventions to achieve a combined good result will be clear from the following.

A measuring device, the measuring principle of which is based on Swedish patent Nos. 75078757-6 and 7613708-2, comprises an automatic balancing function according to Swedish patent application No. 781344-4, and is signal-processed in accordance with the present invention. Taken together this provides a sophisticated and efficient measuring and/or control device, in which inventions, which are independent per se, together form a totality, for example a system function, which in turn is able to provide, for example, billet-treating machines (e.g. grinding machines) with information as to defects, etc., on the surface of the billet.

FIG. 2 shows that especially signals/signal components, which have a small differential coefficient in relation to the fault signal (11), are particularly adapted to be suppressed. This can also be expressed such that low-frequency signals are well suited to be suppressed-/attenuated.

As the signal-delay element, a pluarlity of circuits may be used. Both digital and analog shift registers are, of course, very suitable, but also computers can be used. In certain cases it may be suitable to realize the whole device, or parts thereof, with the aid of a computer, for example, or some other type of programmable electronic equipment. Especially when employing eddy current technique (OFP) for detecting, for example, defects in different materials, the device has a given field of application since, for example, the transducer design can be simplified while at the same time the performance is improved.

By varying the time-lag delay ($t_d$) of the delay circuit, the device can be made selective for different types of defects.

A large field of application of the invention is the detection of cracks on so-called hot billets, where the varying distance of the transducer to the surface of the billet is often a disturbing problem but which can be effectively overcome by means of the invention.

Finally, some clarifying remarks.

By object are meant, for example, bodies, liquids, gases, powders, billets, wire, etc.

By change/irregularity are meant, for example, defects (such as cracks), dimensional changes, speed variations, material changes etc.

By signals referring to the same part, for example point of measuring, on or in the object are meant, for example, signals which during the relative movement of the transducer across the surface of the object, for each point in time, refer to/originate from the part/point of the object which the transducer is currently scanning (at the respective point in time).

By combined signals is meant, for example, that signals are weighted, summed, subtracted, the quotient thereof formed, and so on, according to the current need for obtaining the desired function and result.

At the same time as the present invention makes it possible to simulate the signal shape and properties of the differential transducer starting from the use of a simple absolute transducer, it can, of course, be claimed that the function obtained by way of the delay technique is to be compared to an advanced filter.

By undesired signal is meant, for example, a signal or a part thereof (e.g. a vector) which is to be suppressed. A typical example of such a signal is a disturbing (varied) position signal, a so-called "lift-off" signal.

The invention can be varied in many ways within the scope of the following claims.

I claim:

1. Apparatus for detecting irregularities in the surface of an object, comprising:
   a transducer adapted to be moved over the surface and provide output signals representative of surface irregularities thereof;
   said output signal comprising a first low frequency signal resulting from the varying distance between the transducer and the surface and a second signal of higher frequency than said first signal and representative of said surface irregularities;
   means for processing said output signal and including parallel first and second channels, said first channel conducting said output signal and said second channel including means for delaying said output signal, said processing means further including means for combining the output signal from said first channel and the delayed output signal from said second channel to essentially remove said low frequency signal and enhance said second signal to produce a measuring output signal representative of said surface irregularities.

2. Apparatus according to claim 1, wherein said means for delaying comprises at least one analog shift register.

3. Apparatus according to claim 1, wherein said means for combining comprises a summation circuit.

4. Apparatus according to claim 1, further comprising means for filtering said measuring output signal.

5. Apparatus according to claim 1, wherein said means for delaying delays said output signal by a period $T_d$.

6. Apparatus according to claim 5, wherein said period $t_d$ is variable in dependence upon the characteristics of the surface irregularities.

7. Apparatus according to claim 1, wherein said means for delaying also inverts said output signal.

8. Apparatus according to claim 7, wherein said means for delaying delays said output signal by a period $T_d$.

9. Apparatus according to claim 8, wherein said period $t_d$ is variable in dependence upon the characteristics of the surface irregularities.

10. Apparatus for detecting irregularities in the surface of an object, comprising:

a transducer adapted to be moved over the surface and provide output signals representative of surface irregularities thereof;

said output signal comprising a first signal having a frequency characteristic of varying lift-off distance between the transducer and the surface and a second signal of higher frequency than said first signal and representative of said surface irregularities;

means responsive to said output signal for generating a delayed and inverted output signal; and means for summing said output signal and said delayed and inverted output signal to essentially cancel said first signal and enhance said second signal representative of surface irregularities.

11. Apparatus according to claim 10, wherein said means for generating delays said output signal by a period $T_d$.

12. Apparatus according to claim 11, wherein said period $t_d$ is variable in dependence upon the characteristics of the surface irregularities.

* * * * *